US005654286A

United States Patent [19]
Hostetler

[11] Patent Number: 5,654,286
[45] Date of Patent: Aug. 5, 1997

[54] NUCLEOTIDES FOR TOPICAL TREATMENT OF PSORIASIS, AND METHODS FOR USING SAME

[76] Inventor: Karl Y. Hostetler, 14024 Rue St. Raphael, Del Mar, Calif. 92014

[21] Appl. No.: 485,025

[22] Filed: Jun. 7, 1995

Related U.S. Application Data

[63] Continuation-in-part of Ser. No. 60,258, May 12, 1993, Pat. No. 5,580,571.

[51] Int. Cl.$^6$ .............. A61K 31/505; A61K 31/52; A61K 31/70
[52] U.S. Cl. .............. 514/47; 514/48; 514/51; 514/256; 514/261; 514/269; 514/861; 514/863; 514/887; 536/26.26; 536/26.7; 536/26.8; 544/242; 544/264
[58] Field of Search ............ 514/47, 48, 51, 514/863, 861, 887, 256, 261, 269; 536/26.26, 26.7, 26.8; 544/242

[56] References Cited

U.S. PATENT DOCUMENTS

| | | |
|---|---|---|
| 2,795,580 | 6/1957 | Khorana et al. . |
| 2,970,139 | 1/1961 | Duschinsky et al. . |
| 3,238,191 | 3/1966 | Myers . |
| 4,088,756 | 5/1978 | Voorhees . |
| 4,146,715 | 3/1979 | Schaeffer . |
| 4,199,574 | 4/1980 | Schaeffer . |
| 4,207,315 | 6/1980 | Voorhees et al. . |
| 4,211,770 | 7/1980 | Voorhees . |
| 4,294,831 | 10/1981 | Schaeffer . |
| 4,297,347 | 10/1981 | Katsunoma . |
| 4,323,573 | 4/1982 | Schaeffer . |
| 4,360,522 | 11/1982 | Schaeffer . |
| 4,634,719 | 1/1987 | Takaishi et al. . |
| 4,758,572 | 7/1988 | Spector et al. . |
| 4,804,651 | 2/1989 | Duvic et al. . |
| 4,897,394 | 1/1990 | Zimmerman et al. . |
| 5,021,437 | 6/1991 | Blumenkopf . |
| 5,068,320 | 11/1991 | Koszalka et al. . |
| 5,089,500 | 2/1992 | Daluge . |
| 5,093,114 | 3/1992 | Rideout et al. . |
| 5,128,458 | 7/1992 | Montgomery et al. . |
| 5,223,262 | 6/1993 | Hostetler et al. . |
| 5,478,928 | 12/1995 | Montgomery et al. . |

FOREIGN PATENT DOCUMENTS

| | | |
|---|---|---|
| 285432 | 10/1988 | European Pat. Off. . |
| 286425 | 10/1988 | European Pat. Off. . |
| 301900 | 2/1989 | European Pat. Off. . |
| 0350287 | 7/1989 | European Pat. Off. . |
| 349242 | 1/1990 | European Pat. Off. . |
| 421739 | 4/1991 | European Pat. Off. . |
| 468119 | 1/1992 | European Pat. Off. . |
| 468866 | 1/1992 | European Pat. Off. . |
| 2401449 | 1/1974 | Germany . |
| 1590500 | 6/1981 | United Kingdom . |
| 2168350 | 6/1986 | United Kingdom . |
| WO 91/19721 | 12/1991 | WIPO . |
| 9314103 | 7/1993 | WIPO . |
| 9323021 | 11/1993 | WIPO . |

OTHER PUBLICATIONS

Carson, D., et al. (1992) Oral antilymphocyte activity and induction of apoptosis by 2–chloro–2'–arabino–fluoro–2'–deoxyadenosine. Proc. Natl. Acad. Sci. 89:2970–2974.

Eibschutz, B., et al. (1995) Oral 2–chlorodeoxyadenosine in psoriatic arthritis. Arthritis & Rheumatism 38(11):1604–1609.

Lesiewicz, J., et al. (1985) Animal screens for retinoids. Models in Dermatology 2:112–116.

Agranoff, B. et al. (1963) Cytidine Diphosphatase – dl – Dipalmitin. Biochem. Prep. 10:47–51.

Ellis, M. et al. (1989) Orofacial infection of athymic mice with defined mixtures of acyclovir–susceptible and acyclovir–resistant herpes simplex virus type 1. Antimicrobial Agents and Chemotherapy 33(3):304–310.

Furman, P. et al. (1979) Inhibition of herpes simplex virus––induced DNA polymerase activity and viral DNA replication by 9–(2–hydroxyethoxymethyl)guanine and its triphosphate. J. Virol. 32:72–77.

Fyfe, J. et al. (1978) Thymidine kinase from herpes simplex virus phosphorylates the new antiviral compound, 9(2–hydroxyethoxymethyl)guanine. J. Biol. Chem. 253:8721–8727.

Gomez–almaguer, D. et al. (1988) Acyclovir in the treatment of aplastic anemia. Amer. J. of Hematology 29:172–173.

King (1988) History, pharmacokinetics, and pharmacology of acyclover. J. Am. Acad. Dermatol. 18:176–179 (Abstract only).

Krenitsky, T. et al. (1990) Nucleotide analogue inhibitors of purine nucleoside phosphorylase. The Journal of Biological Chemistry 265(6):3066–3069.

Lobe, D. et al. (1991) Synergistic topical therapy by acyclovir and A11OU for herpes simplex virus induced zosteriform rash in mice. Antiviral Research 15:87–100.

Masch et al. (1965) Nivea, the Prototype of Lanolin Absorption Creams. A history of Nivea Cream. American Perfumer and Cosmetics 80:35–38.

Merta et al. (1990) Inhibition of herpes simplex virus DNA polymerase by diphosphates of acyclic phosphonylmethoxyalkyl nucleotide analogues. Antiviral Research 13:209–218.

O'Brien, W. et al. (1990) Nucleoside metabolism simplex virus–infected cells following treatement with interferon and acyclovir, a possible mechanism of synergistic antiviral activity. Antimicrob. Agents and Chemother. 34(6):1178–1182.

(List continued on next page.)

*Primary Examiner*—James O. Wilson
*Attorney, Agent, or Firm*—Knobbe, Martens, Olson & Bear

[57] ABSTRACT

Typical treatment of psoriasis and other diseases of skin cell hyperproliferation using pharmaceutical compositions containing mono-, di, and tri-phosphate esters of antiproliferative nucleoside analogs and related analogs, DNA chain-terminating dideoxynucleosides and other nucleoside analogs. The useful phosphate esters include phosphoramidates and phosphothiorates, as well as polyphosphates having C and S bridging atoms.

40 Claims, No Drawings

OTHER PUBLICATIONS

Ott, D.G. et al. (1967) Chemical synthesis of nucleoside triphosphates. Anal. Biochem. 21:469–472.

Remington's Pharmaceutical Sciences, 15th Edition., 175. Mack Publishing Company., Easton, Pennsylvania 18042. (Chapter 87: Blaug. Seymour).

Rune, S.J. et al. (1990) Acyclovir in the prevention of duodenal ulcer recurrence. Gut 31:151–152.

Spruance, S. et al. (1982) Treatment of herpes simplex labialis with topical acyclovir in polyethylene glycol. J. Infect. Dis. 146:85–90.

Spruance, S. et al. (1984) Early patient–initated treatment of herpes labialis with topical 10% acyclovir. Antimicrob. Agents Chemother. 25:553–555.

Straus, S. (1989) Effect of oral acyclovir treatment on symptomatic and asymptomatic virus shedding in recurrent genital herpes. Sexually Transmitted Diseases 16(2):107–113.

Toorchen, D. et al. (1983) Mechanisms of chemical mutagenesis and carcinogenesis: effects on DNA replication of methylation at the O6–guanine position of dGTP. Carcinogenesis 4:1591–1597.

Welch, C.J. et al. (1985) The chemical synthesis and antiviral properties of an acyclovir–phospholipid conjugate. Acta Chemica Scandinavica B39:47–54.

Whitley, R. et al. (1990) Immunobiology and Prophylaxis of Human Herpevirus Infections, C. Lopez (ed). Plenum Press, New York pp. 243–253.

Yoshikawa, M. et al. (1969) Phosphorylation. III. Selective phosphorylation of unprotected nucleosides. Bull. Chem. Soc. Japan 42:3505–3508.

Yoshikawa, et al. (1967) A novel method for phosphorylation of nucleosides to 5'–nucleotides. Tetrahedron Lett., 50:5065–5068.

Bauer, E., et al. (1989) Psoriasis and other proliferative disorder of epithelium. In Textbook of Internal Medicine, W.N. Kelly (ed.) pp. 1042–1045.

Chan, E, et al. (1982) Total synthesis of (8R)–3–(2–deoxy–β–D–erythro–pentofuranosyl)–3,6,7,8–tetrahydroimidazol[4,5–d][1,3]diazepin–8–ol . . . J. Org. Chem. 47:3457–3464.

Fox, J., et al. (1958) Thiation of Nucleosides. I. synthesis of 1–Amino–6–mercapto–9–β–D–ribofuranosylpurine ("thioguanosine") and related purine nucleosides. J. Am. Chem. Soc. 28:1669–1675.

Grove, G. (1979) Epidermal cell kinetics in psoriasis. J. Dermatol. 18:111–122.

Gutowski, G., et al. (1973) Pyrazomycin B: isolation and characterization of an α–C–nucleoside antibiotic related to pyrazomycin. Biochemical and Biophysical Research Communications 51(2):312–317.

Henderson, J. and Paterson, A., Nucleoside Metabolism (Academic Press, 1973) New York pp. 266–271.

Hoard, D., et al. (1965) Conversion of mono– and oligodeoxyribonucleotides to 5'–triphosphates. J. Am. Chem. Soc. 87(8):1785–1788.

Hunt, B., et al. (1967) Methods, apparatus: new product reasearch, process development and design. Chemistry and Industry pp. 1868–1869.

Hutchinson, D. (1991) The synthesis, reactions, and properties of nucleoside mono–, di–, tri–, and tetraphosphates and nucleotides with changes in the phosphoryl residue. In Chemistry of Nucleotides and Nucleosides, (L. Townsend, ed.), pp. 81–1460.

Lowe, N. (1988) Psoriasis: in vivo models for topical drug evaluation. Drug Development Research 13:147–155.

McDonald, C. (1981) The uses of systemic chemotherapeutic agents in psoriasis. Pharmac. Ther. 14:1–24.

Moffatt, J., et al. (1961) Nucleoside polyphosphates. XII. The total synthesis of Coenzyme $A^2$. J. Am. Chem. soc. 83:663–675.

Myers, T., et al. (1963) Phosphonic acid analogs of nucleoside phosphates. I. the synthesis of 5'–adenylyl methylenediphosphonate, a phosphonic acid analog of ATP. J. of Am. Chem. Soc. 85:3295–3295.

Robins, R., et al. (1963) Aromaticity in heterocyclic systems. I. the synthesis ans structure of certain 4'6–dihydroxyimidazo[4,5–c]pyridines. J. Org. Chem. 28:3041–3046.

Robins, R., et al. Purines and purine nucleoside analogues as antitumor agents. in The Chemistry of Antitumor Agents. D.E.V. Wilman, ed. (1990) Blackie London. pp. 300–321.

Seela, F., et al. (1992) 7–deazapurine containing DNA: efficiency of $C^7G_dTP$, and $C^7A_dTP$ and $C^7I_dTP$ incorporation during PCR–amplification and protection from endodeoxyribonuclease hydrolysis. Nucleic Acids Research 20(1):55–61.

Sundberg, J., et al. (1989) The flaky skin (fsn) mutation, chromosome! J. Invest. Dermatol. 92:414.

van Boom, J., et al. (1975) 2,2,2–tribromoethyl phosphoromorpholinochloridate: a convenient reagent for the synthesis of ribonucleoside mono–, di– and tri–phosphates.

Yount, R. G. ATP analogs. in Advances in Enzymology, (F.F. Nord ed. 1975) J. Wiley, New York, 43:1–56.

NUCLEOTIDES FOR TOPICAL TREATMENT OF PSORIASIS, AND METHODS FOR USING SAME

This application is a continuation-in-part of U.S. patent application Ser. No. 08/060,258, filed May 12, 1993, now U.S. Pat. No. 5,580,571.

FIELD OF THE INVENTION

The present invention relates to the topical treatment of psoriasis and other diseases caused by hyperproliferation of skin cells. Specifically, the invention relates to methods of treatment of psoriasis and other skin diseases with formulations containing phosphate esters of nucleoside analogs, antiproliferative nucleosides and DNA chain-terminating dideoxynucleosides.

BACKGROUND OF THE INVENTION

Psoriasis is a benign disease of human skin generally characterized by plaques covered by thickened scales. The disease is caused by increased proliferation of epidermal cells of unknown cause. In normal skin the time required for a cell to move from the basal layer to the upper granular layer is about five weeks. In psoriasis, this time is only 6 to 9 days, partially due to an increase in the number of proliferating cells and an increase in the proportion of cells which are dividing (G. Grove, *Int. J. Dermatol.* 18:111, 1979). Approximately 2% of the population the United States have psoriasis, occurring in about 3% of caucasian Americans, in about 1% of African Americans, and rarely in native Americans.

Epidermal hyperplasia associated with inflammation is characteristic of psoriatic skin. Skin biopsies of affected areas show hyperkeratosis with retention of nuclear fragments, increased proliferation with defective keratinization, and chronic inflammatory infiltrates. (E. A. Bauer, M. Tabas and J. B. Goslen, in *Textbook of Internal Medicine*, W. N. Kelly (ed.), 1989, pp 1042–1045). With increased cell proliferation, there is increased DNA synthesis in the affected tissue which has been the basis for assays for evaluating the efficacy of anti-psoriasis agents.

There is no true animal model for psoriasis although rare primates with clinical and histopathological features of psoriasis have been reported (N.J. Lowe, *Drug Dev. Res.* 13:147–155, 1988). Consequently, investigation of anti-psoriasis drugs has relied on experimentally-induced hyperplasia in animals or a mouse strain bearing the spontaneous mutation (fsn) for flaky skin (J. P. Sundberg et al., *J. Invest. Dermatol.* 92:414, 1989). Another mouse model having epidermal proliferation is the essential fatty-acid deficient (EFAD) hairless mouse.

Experimentally induced animal models also include athymic nude mice, which are immunologically defective, engrafted with diseased human skin.

Current therapies consist of efforts to reduce the rapid cell proliferation and to reduce inflammation. These therapies include use of active agents topically, systemically or both, which can be combined with irradiation. Topical treatments include use of steroid creams, and use of coal tar ointments followed by ultraviolet irradiation (UV B, 290–320 nm). Topical 5-fluorouracil has been used with some success but the treatment causes severe erythema, edema, bullae formation and ulceration of the skin in treated areas and therefore is not well accepted by patients (C. J. McDonald, *Pharmac. Ther.* 14:1–24, 1981). TRIAZURE™ (6-azauridine triacetate) has been tested topically on the skin of patients with psoriasis but was without effect (William Drell, personal communication, May, 1993).

Antiproliferative agents, including methotrexate, 6-azauridine and triazure, have also been used systemically. Extensive psoriasis has been treated with oral administration of 8-methoxypsoralen, a photosensitizer, followed by ultraviolet A (320 nm) irradiation or administration of retinoids, such as etretinate, followed by ultraviolet A irradiation (C. J. McDonald, *Pharmac. Ther.* 14:1–24, 1981; E. A. Bauer, M. Tabas, and J. B. Goslen, in *Textbook of Internal Medicine*, W. N. Kelly (ed.), 1989, pp 1042–1045).

Other diseases caused by hyperproliferation of skin cells include atopic dermatitis, lichen planus, actinic keratosis, basal cell carcinoma and squamous cell carcinoma. The topical use of phosphate esters of antiproliferative nucleosides and dideoxynucleosides and their analogs has not been reported for treating psoriasis or other diseases caused by hyperproliferation of skin cells.

Copending U.S. patent application (Ser. No. 08/060,258, hereby incorporated by reference) discloses that phosphate esters of antiherpes nucleosides, such as acyclovir, are effective in animals infected with mutant virus strains in which acyclovir cannot be converted to acyclovir phosphates due to a mutation affecting the vital enzyme, thymidine kinase.

SUMMARY OF THE INVENTION

According to the invention there is provided a method of treatment for psoriasis and other diseases caused by hyperproliferation of skin cells, comprising applying topically a composition containing as an active ingredient a nucleoside analog phosphate ester having the formula:

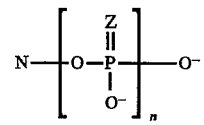

wherein N is a nucleoside analog that has antiproliferative activity; Z is O or S or NH; and n is 1, 2, or 3; or a non-toxic pharmaceutically acceptable salt thereof. The method may also be carried out using a composition containing as an active ingredient a nucleoside analog phosphate ester having the formula:

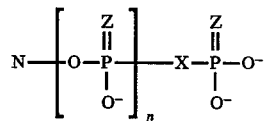

wherein N is a nucleoside or nucleoside analog that has antiproliferative activity; X is O or $CH_2$ or S; Z is O or S or NH; and n is 2; or a non-toxic pharmaceutically acceptable salt thereof.

In preferred embodiments the nucleoside or nucleoside analog is selected from the group consisting of cytosine arabinoside, guanosine arabinoside, 5-fluorodeoxyuridine, 5-fluorouridine, 6-azauridine, 2-chlorodeoxyadenosine, 2-arabino-chloro-2'-fluoroaradeoxyadenosine, 9-(β-D-arabinofuranosyl)-2-fluoroadenine, 6-methylmercaptopurine riboside, dideoxycytidine, dideoxythymidine, dideoxyguanosine, dideoxyinosine, dideoxyadenosine, 2'-deoxytubercidin, 2'-deoxyformycin, 2'-deoxy-(3,4-d)pyrimidine, acyclovir and ganciclovir.

According to the method of the invention, the active ingredient in the composition is in a concentration of 0.001 gm % to 100 gm %. In a preferred embodiment, the active ingredient in the composition is in a concentration of 0.01 gm % to 10 gm %. In a particularly preferred embodiment, the active ingredient in the composition is in a concentration of 0.1 gm % to 5 gm %.

According to one aspect of the invention, the composition is applied to an area of skin from one to ten times daily in a dosage of 0.001 gm % to 100 gm % per application. Alternatively, the composition is applied to an area of skin from one to ten times daily in a dosage of 0.01 gm % to 10 gm % per application. In a preferred embodiment, the composition is applied to an area of skin from one to ten times daily in a dosage of 0.1 gm % to 5 gm % per application.

According to yet another aspect of the invention there are provided pharmaceutical compositions comprising as an active ingredient a nucleoside analog phosphate esters of the method. In preferred embodiments, the pharmaceutical compositions further comprise propylene glycol, polyethylene glycol 400 and polyethylene glycol 3350. In particularly preferred embodiments, the pharmaceutical compositions further comprise an ingredient for enhancing penetration of the skin during topical application.

The invention also provides antiproliferative nucleoside analogue phosphate esters used in the methods of the invention. In a preferred embodiment the nucleoside analogue is a phosphoramidate or phosphothiorate ester and/or is a methylene phosphonate or a thiophosphonate ester.

DETAILED DESCRIPTION OF THE INVENTION

The invention provides phosphate esters of antiproliferative nucleosides such as 2-chlorodeoxyadenosine, arabino-2-chloro-2'-fluoroaradeoxyadenosine, cytosine or guanosine arabinoside, 6-azauridine, 6-mercaptopurine riboside, 5-fluorouridine, 5-fluorodeoxyuridine, acyclovir, gancyclovir, dideoxycytidine and other dideoxynucleosides and chain-terminating nucleoside analogs which when applied topically are surprisingly and unusually effective in reducing the rate of cell proliferation and depleting lymphocytes in psoriatic skin.

The monophosphate, diphosphate and triphosphate esters have the general formula

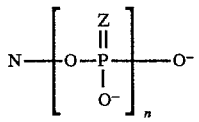

wherein N is an antiproliferative nucleoside analog; Z is O, S, or NH; and n is 1, 2 or 3; or alternatively have the following formula

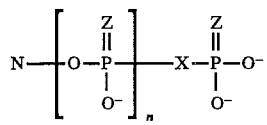

wherein
N is an antiproliferative nucleoside analog;
Z is O, S or NH;
X is O, $CH_2$ or S; and
and n is 1 or 2.

Accordingly, the phosphoesters can be phosphate, phosphothiorate, or phosphoramidate, and the diesters and triesters may have bridging atoms other than oxygen, for example, 2,3-µ-thiotriphosphate esters, or 2,3-µ-methylenediphosphonate.

Contrary to expectation, these nucleoside analog phosphates can surprisingly pass through the cell membrane of hyperproliferative skin cells and reduce the rate of cell division by inhibiting various enzymatic steps in the biosynthesis of purines and pyrimidines, nucleotides, RNA and DNA. Also, the compounds 2-chlorodeoxyadenosine phosphate and 2-chloro-2'-arabino-fluoroaradeoxyadenosine phosphate are particularly useful in treating the inflammatory component of psoriasis because of their ability to inhibit growth of lymphocytes and mononuclear white blood cells present in inflammatory infiltrates in the skin of psoriasis patients. The invention also provides for pharmaceutical formulations of the nucleoside analog mono-, di- and triphosphates in concentrations that can be applied topically to effectively reduce the proliferation of psoriatic skin cells. DNA chain-terminating dideoxynucleoside phosphates, when applied to the skin in a suitable topical formulation, will similarly reduce proliferation of psoriatic cells. These include acyclovir, ganciclovir, dideoxycytidine, dideoxythymidine, dideoxyguanosine, dideoxyadenosine, dideoxyinosine, 3'-azidodideoxythymidine (AZT) and other dideoxynucleoside analogs such as those described in copending U.S. patent application Ser. No. 07/373,088 which is hereby incorporated by reference.

Additional phosphate esters of nucleosides useful as antipsoriasis agents when administered topically include those listed in *Nucleotide Metabolism* (J. F. Henderson & A. R. P. Paterson, Academic Press, 1973, at pp. 266–271).

Salts of these compounds can be easily prepared and such salts should exhibit enhanced solubility in aqueous media, i.e., cream, gels, or other aqueous dispersions. Typically, useful salts of these compounds include sodium, potassium, lithium, ammonium, or hydrogen salts. Any physiologicallly acceptable cation known to those skilled in the art may also be used. Moreover, such salts are usable and effective in polyethylene glycol creams and lotions which provide a favorable mucosal or cutaneous dispersion.

Topical Compositions

According to another aspect of the invention, a method is provided for topical treatment of psoriasis, comprising applying a composition containing the nucleoside analog phosphate esters of the invention to the psoriatic lesions on the skin of an affected patient.

The nucleoside analog phosphate esters, dideoxynucleoside and chain-terminating nucleoside phosphate esters of the invention as previously described can be prepared for topical use by incorporation into a variety of compositions known to those in the art as useful and convenient for dermatological use. The nucleoside phosphate esters are often more water soluble than the corresponding bases and accordingly an aqueous solution, water-in-oil emulsion, or an aqueous cream may be highly preferred formulations. Water solubility of the nucleoside analog phosphate esters of the invention can be enhanced through the preparation of salts, such as sodium, potassium, lithium ammonium, or hydrogen. In a particularly preferred composition, the active ingredient is prepared in a polyethylene glycol (PEG) vehicle. Alternatively, the active ingredients can be topically applied in a dry powder formulation, using an insoluble powder, such as starch or talc as a diluent or carrier.

The vehicle is an important component of some topical compositions, because it can be selected to enhance penetration, to prolong the duration of activity, or to meet requirement of the site of application. For example, a formulation for application to the callous parts of the body, such as the palms of the hand or bottoms of the feet, can include a penetration enhancing agent such as dimethylsulfoxide, propylene glycol or AZONE™. Alternatively, a powdered composition can be selected for application to the intertriginous zones such as the crotch, inner elbow or between the fingers or toes. The composition can also be made up to contain various organic polymers or other compositions known to those of skill in the art to give sustained release of the active anti-psoriasis derivatives.

A multitude of appropriate topical compositions can be found in the formulary known to all pharmaceutical chemists: Blaug, S., Ch. 87 in *Remington's Pharmaceutical Sciences* (15th Ed., 1975, Mack Publishing Company, Easton, Pa. 18042). These compositions include for example, powders, pastes, ointments, jelly, waxes, oils, lipids, anhydrous absorption bases, oil-in-water or water-in-oil emulsions, emulsions carbowax (polyethylene glycols of a variety of molecular weights), semi-solid gels, and semi-solid mixtures containing carbowax.

The concentration of active ingredient in the topical compositions of the invention can be from about 0.001 gm % to 100 gm %; preferably from about 0.01 gm % to 10 gm %; most preferably from about 0.1 gm % to about 5 gm %. The compositions can further comprise effective concentrations of other agents which help to promote penetration of the skin and healing, as described in the above-referenced formulary and are well known to those of ordinary skill in the art.

Efficacy of topical compositions containing the active nucleoside analog phosphates of the invention can be evaluated using conventional testing procedures, known to those skilled in the art. These include use of simulated animal models (e.g., epidermal hyperplasia) and other predictive in vivo assays (N. J. Lowe, *Drug Dev. Res.* 13:147–155, 1988).

The compositions can be applied to the psoriatic lesions of the affected skin repeatedly; for example once, twice, or several times a day, and the treatment can be extended for several days until healing is achieved. The risk of incidence of toxicity and irritation is minimal.

In particularly preferred embodiments of the invention the nucleoside consists of 2-chlorodeoxyadenosine, 2-chloro-2'fluoro-ara-adenosine, 6-azauridine, 5-fluorouridine or 5-fluorodeoxyuridine, guanosine arabinoside or a dideoxy-nucleoside and a topical cream consisting of a mixture containing polyethylene glycol 3350, polyethylene glycol 400 and propylene- or ethylene glycol.

Nucleoside analogues consist of cytosine or guanosine arabinoside, 5-fluorodeoxyuridine, 5-fluorouridine, 6-azauridine and DNA chain-terminating dideoxynucleosides such as dideoxycytidine, dideoxythymidine, dideoxyguanosine, dideoxyinosine, and dideoxynucleoside analogs, as described in copending U.S. patent application Ser. No. 07/373,088 filed Jun. 28, 1989, now U.S. Pat. No. 5,223,263; and related compounds 2-chlorodeoxyadenosine and 2-chloro-2'-arabino-fluorodeoxyadenosine and 9-(β-D-arabinofuranosyl)-2-fluoroadenine. Additional nucleoside analogs that inhibit the DNA polymerase of epidermal cells when delivered as mono-, di-, or tri-phosphates include 2'-deoxytubercidin, 2'-deoxyformycin, and 2'-deoxy-(3,4-d) pyrimidine.

Additional compounds useful as anti-psoriasis agents when administered topically include the mono-, di- and tri-phosphate esters of the ribonucleoside and deoxyribonucleoside derivatives of 8-azaguanine, 6-mercaptopurine, 6-thioguanine, 6-methylmercaptopurine, 2,6-diaminopurine, 8-azaxanthine, formycin, psicofuranine, decoyinine, xylosyladenine, 6-chloropurine, 6-azauracil, 5-fluorocytidine or 5-fluorocytosine, 5-fluorouracil, 5-iodouracil and 5-bromouracil; and the mono-, di- and tri-phosphate esters of 3'-deoxyadenosine, deoxyxylopyranosylthymine, deoxyglucopyranosylthymine and cytosine arabinoside (for chemical structures, see *Nucleotide Metabolism*, J. F. Henderson & A. R. P. Paterson, Academic Press, 1973, at pp. 266–271).

Assays for Topical Drug Evaluation

1. Epidermal DNA Synthesis Suppression Assay. Because increased DNA synthesis is characteristic of epidermal hyperplasia in psoriatic skin, the incorporation of radioactive DNA precursors into skin tissue treated with a pharmacological agent has been used to evaluate the degree of suppression of DNA synthesis caused by the pharmacological agent. Briefly, an anti-psoriasis agent in a topical carrier is applied to the area of an athymic mouse where psoriatic human dermis and epidermis has been engrafted using techniques well known in the art. Similarly the EFAD hairless mouse model can be used in this assay to measure the effects of anti-proliferative drugs. About 6 hours after treatment, the treated tissue is excised and placed into tissue culture medium containing $^3$H-thymidine deoxyribose or $^3$H-bromodeoxyuridine for pulse labeling for 0.1–5 hours. Then the DNA is isolated from the tissue using standard procedures and the incorporation of $^3$H-thymidine deoxyribose or $^3$H-bromodeoxyuridine into the DNA is measured by determining the radioactivity (cpm/μg of DNA) in the isolated DNA. The efficacy of the anti-psoriasis agent for proliferative suppression is determined by comparing the incorporation of radioactivity into DNA from untreated tissue with that of DNA from tissue treated with different compositions (increasing % of active ingredient) of the anti-psoriasis agent.

2. Polyamine Biosynthesis Inhibition Assay. This assay is based on the amount of ornithine decarboxylase (ODC) present in epidermal cells. ODC is the rate-limiting enzyme in the formation of polyamines which are generally elevated in hyperplasia including epidermal hyperplasia associated with psoriasis. Increased ODC activity can also be induced by stratum corneum tape stripping (Lesiewicz, et al., in *Models in Dermatology*, vol. 2, pp. 112–116 (H. I. Maibach & N. J. Lowe, eds.), 1985) or by application of a phorbol ester (12-O-tetradecanoylphorbol-13-acetate or TPA)

3. Skin biopsy. The EFAD hairless mouse, the fsn/fsn flaky skinned mouse, or an athymic mouse engrafted with psoriatic human skin is treated with a anti-psoriatic pharmaceutical and within 1–15 days the treated skin is examined for gross indications of psoriasis (flakiness of skin, redness of inflammation, etc.) and then analyzed by biopsy so that the number of epidermal cell layers can be counted under a microscope using standard histological procedures. The number of epidermal cell layers is compared to similarly examined normal and untreated psoriatic skin to determine the effect of the treatment with the anti-psoriatic pharmaceutical. Also, the relative degree of inflammation in the tissue can be quantitated by determining the number of white blood cells (i.e., neutrophils and/or monocytes) in the capillaries of the dermis and the dilation of the capillaries relative to untreated psoriatic skin and normal control skin.

Similarly, human clinical trials using skin biopsy and microscopic examination can be done using bilateral paired comparisons with small quantities of anti-psoriatic pharmaceutical agents applied to areas of the skin (e.g., on the forearms or legs) of about 3 cm in diameter. Bilateral paired comparisons are particularly preferred to avoid the risk of a cross-over effect from a treated area into a non-treated control area.

4. Use of the Flaky Skin Mouse. Mice inbred for the spontaneous flaky skin mutation (fsn/fsn) develop white scaly skin after weaning that becomes progressively thicker with age, thus resembling proliferative skin diseases, in particular psoriasis. By 42 days of age, mice show epidermal hyperplasia with a multilaminated basement membrane and inflammation as measured by increased white blood cells and tortuous dermal blood vessels, all characteristic of human psoriasis. These mice can serve as a model of human psoriasis for determining the efficacy of treatment using topically applied nucleoside phosphate. A composition including the nucleoside phosphate is applied to a 1–5 mm portion of the dorsal or ventral skin of a fsn/fsn mouse and the skin is observed grossly and microscopically from 12 hr to 15 days later to determine the degree of epidermal hyperplasia and other symptoms of psoriatic skin presented above using standard dermatological and histological methods. The relevant comparisons are to a similar portion of the mouse that was not treated, to another fsn/fsn mouse that was not treated, to a fsn/fsn mouse treated with just the carrier ingredients without the nucleoside phosphate and to non-mutant mice for the fsn locus similarly treated.

5. Keratinocyte markers. Changes in protein expression are consistent with changes in hyperplasia associated with psoriatic skin. Two molecules useful for detecting abnormal conditions in the skin are keratin and filaggrin. Accumulation of the mouse-specific keratin, K6, in the suprabasilar epidermis is a molecular change typically associated with hyperplasia. In the hairless EFAD mouse or fsn/fsn mouse, antibody-based methods of detecting K6 are useful for determining the presence and amount of the molecule in the suprabasilar epidermis and thus can serve as an indicator of efficacy of anti-psoriasis compositions.

Filaggrin is a protein in the epidermis which normally is associated with keratohyalin granules in the stratum granulosum and in transitional cells but which disappears in upper cornified cells. However, in the fsn/fsn mouse, filaggrin remains present in the superficial cell layers in a pattern characteristic of transitional cells. Thus the presence of filaggrin in upper cornified cells, as detected by anti-filaggrin antibodies and/or microscopic inspection, is characteristic of psoriatic cells and can be used to evaluate the efficacy of anti-psoriasis pharmaceutical preparations applied to the skin of the fsn/fsn mouse.

Synthesis of selected purines and purine nucleoside analogs. Specific methods of synthesizing some antiproliferative purines and purine nucleoside analogs useful as phosphate esters for the treatment of psoriasis are summarized. Additional compounds and methods of synthesis are known to those skilled in the art. Representative procedures are disclosed in R. K. Robins and G. D. Kini, in *The Chemistry of Antitumour Agents* (D. E. V. Wilman, ed.), 1990, at pp.299–321.

(1) Purine analogs

6-Mercaptopurine synthesis is accomplished by treatment of hypoxanthine with phosphorus pentasulphide in tetralin at elevated temperature.

6-Thioguanine is synthesized by treatment of guanine with phosphorus pentasulphide in refluxing pyridine.

3-Deazaadenine, 3-deazahypoxanthine and 3-deaza-6-mercaptopurine are synthesized by ring closure of the appropriately substituted 3,4-diaminopyrimidines in the imidazo [4,5-c]pyridine ring system (Robbins, R. K. et al., J. Org. Chem. 28:3041, 1963).

3-Deazaguanine is synthesized when methyl 5(4)-carbamoylmethylimidazole-4(5)-carboxylate is dehydrated with phosphorus oxychloride to produce methyl 5(4)-cyanomethylimidazole-4(5)-carboxylate which is cyclised upon treatment with liquid ammonia.

(2) Purine Nucleosides

6-Methylmercaptopurine riboside is synthesized by condensing 6-methylmercaptopurine with 2,3,5-tri-O-acetyl-D-ribo-furanosyl chloride using the catalyst mercuric chloride followed by deacetylation. Alternatively, 6-methylmercaptopurine riboside can be produced directly by methylation of 6-thioinosine (Fox, J. J. et al., J. Am. Chem. Soc. 80: 1669, 1958).

9-$\beta$-D-Arabinofuranosyl adenine (ara-A) is synthesized when the 3',5'-di-O-isopropylidene derivative of 9-($\beta$-D-xylofuranosyl)adenine is treated with methanesulphonyl chloride to convert it to the corresponding 2'-O-mesyl derivative, which is cleaved by acetic acid to produce 9-(2'-O-mesyl-$\beta$-D-xylofuranosyl)adenine, which is treated with sodium methoxide in methanol to produce the 2',3'-epoxide, which is treated with sodium in aqueous dimethylformamide to open the ring and produce ara-A which is purified by crystallization.

The related compound, 9-$\beta$-D-arabinofuranosyl-2-fluoroadenine (2-fluoro-ara-A) is synthesized by acetylating 2,6-diaminopurine with acetic anhydride in refluxing pyridine to produce 2,6,-diacetamidopurine, which is condensed with 2,3,5-tri-O-benzyl-$\alpha$-D-arabinofuranosyl chloride to produce the blocked $\beta$-anomer nucleoside, which is deacetylated by treatment with methylamine in ethanol to produce diamino nucleoside, which is treated with a mixture of fluoboric acid and tetrahydrofuran with aqueous sodium nitrate to produce 2',3',5'-tri-O-benzyl-$\beta$-D-arabinofuranosyl-2-fluoroadenine, which is treated with boron trichloride to produce 2-fluoro-ara-A.

2-Chloro-2'-deoxyadenosine is synthesized by fusing 2,6-dichloropurine with 1,3,5-tri-O-acetyl-2-deoxy-D-erythropentofuranose and by other methods (Robins and Kini, in *The Chemistry of Antitumour Agents*, 1990, at p 308).

(3) Purine Cyclic Nucleotides and Cyclic Nucleotide Analogs

8-Chloro-cAMP is synthesized by bromination of cAMP in the presence of aqueous sodium hydroxide to produce 8-bromo-cAMP, which is treated at elevated temperatures with thiourea to produce 8-thio-cAMP, which is chlorinated with chlorine gas in a solution of methanolic HCl.

(4) Other Anti-Proliferative Nucleosides Related to Purines

Tiazofurin (2-$\beta$-D-ribofuranosyl-thiazole-4-carboxamide is synthesized by treating 2,5-anhydro-3,4,6-tri-O-benzoyl-D-allonothioamide with ethylbromopyruvate to promote ring closure producing ethyl 2-(2,3,5-tri-O-benzoyl-$\beta$-D-ribofuranosyl)thiazole-4-carboxylate as the major product, which is separated and treated with methanolic ammonia.

A related compound, selenotiazofurin, is synthesized by treatment of 2,5-anhydro-3,4,6-tri-O-benzoyl-D-allononitrile with liquid $H_2Se$ to produce the corresponding selenamide, which is reacted with ethylbromopyruvate to promote ring closure producing ethyl 2-(2,3,5-tri-O-benzoyl-$\beta$-D-ribofuranosyl)selenazole-4-carboxylate as the major product, which is treated with methanolic ammonia.

Pyrazofurin (3-(1-β-D-ribofuranosyl)-4-hydroxyprazole-5-carboxamide) is a naturally occurring nucleoside that can be isolated from *Streptomyces candidus* (Gutowski, G. E. et al., Biochem. Biophys. Res. Commun. 51: 312, 1973). Alternatively pyrazofurin is synthesized by treatment of the α-keto ester with the hydrazine derivative to produce the diazo intermediate, which is heated with acetic anhydride and sodium acetate to produce cyclised hydroxypyrazole nucleoside, which is aminated with methanolic ammonia and then debenzylated to produce pyrazofurin.

2-Deoxycoformycin (8R)-3-(2-deoxy-β-D-erythropentofuranosyl)-3,6,7,8-tetrahydroimidazo[4,5-d][1,3]-diazepin-8-ol is synthesized by glycosylation of the aglycon, 6,7-dihydroimidazo[4,5-d][1,3]-diazepin-8(3H)-one with 2-deoxy-3,5-di-O-p-toluoyl-D-erythropentofuranosyl chloride (Chan, E. et al., J. Org. Chem. 47: 3457, 1982).

Synthesis of Nucleoside Monophosphates, Diphosphates and Triphosphates and Nucleoside Phosphate Analogues: The methods for synthesizing nucleoside monophosphates by reacting the nucleoside with phosphorus oxychloride are described in copending U.S. patent applications Ser. No. 07/373,088 and Ser. No. 08/060,258 and as previously described (Yoshikawa et al., *Bull. Chem. Soc. Japan* 42:3505–3508, 1969; Toorchen, D. and Topal, M., *Carcinogenesis* 4:1591–1597, 1983). Nucleoside diphosphates are prepared by the method of Ott, D. G. et al. (*Anal. Biochem.* 21:469–472, 1967).

Nucleoside triphosphates are prepared by the method of Seela and Röling (*Nuc. Acids Res.* 20:55–61, 1992), or from the nucleoside monophosphates by the method of Moffat and Khorana (*J. Am. Chem. Soc.* 83:663, 1991), or by the method of Hoard and Ott (*J. Am. Chem. Soc.* 87:1785–1788, 1963). Examples 1–3 below present the details of some syntheses useful for preparing phosphate esters of nucleosides and nucleoside analogs.

Other nucleoside phosphate analogues including nucleoside phosphorothioates, nucleoside phosphoramidates, nucleoside phosphonates and nucleoside phosphorofluoridates can be synthesized using methods well known to those skilled in the art and summarized, for example, by D. W. Hutchinson (The synthesis, reactions and properties of nucleoside mono-, d-, tri-, and tetraphosphates and nucleotides with changes in the phosphoryl residue. In *Chemistry of Nucleotides and Nucleosides*, L. Townsend, ed., 1991 at pp 81–146 and references therein). The common syntheses are summarized as follows.

(1) Nucleoside Phosphorothioates are analogues of nucleotides in which one or more of the phosphoryl oxygen atoms have been replaced by sulfur. Early methods of synthesis reacted a protected nucleoside and tris(1-imidazolyl) phosphane sulfur whereas more recent syntheses replace the latter reagent with thiophosphoryl-chloride ($PSCl_3$). A nucleoside phosphoranilidate can be converted into a phosphorothioate by treatment with sodium hydroxide and carbon disulfide. Nucleoside 5'-phosphorothioates can result from direct sulfurization of nucleoside 5'-phosphites. Purine nucleoside 2'(3')-phosphorothioates can be synthesized by reacting their 2',3'-O-di-n-butylstannylene derivatives with thiophosphoryl chloride followed by alkaline hydrolysis.

(2) Nucleoside Phosphoramidates are analogues in which one or more phosphoryl oxygen atoms have been replaced by nitrogen creating a P—N bond which is considerably more labile than the P—S bond of nucleoside phosphorothioates even under mildly acidic conditions. Syntheses of these compounds include the phosphorylation of amino-nucleosides and the treatment of nucleoside azides with triesters of phosphorous acid. Lipophilic nucleoside phosphoramidates may be particularly useful anti-psoriatic compounds because of their ability to be more readily taken up by cells where they are hydrolyzed into biologically active compounds.

(3) Nucleoside Phosphonates are compounds in which a phosphoryl oxygen is replaced by carbon creating a stable P—C bond and having decreased acidity of the P—OH groups when the phosphorus atom is substituted with an electron-donating alkyl group in place of the oxygen. Nucleoside phosphonates are easily prepared from nucleoside halides by those skilled in the art using either the Arbusov or the Michaelis-Becker reactions. Nucleoside 5'-phosphonates can be synthesized from 2',3'-protected 5'iodo-5'-deoxynucleosides using methods well known to those skilled in the art. Isosteric nucleoside 5'-phosphonates, in which the 5'-oxygen is replaced with a methylene group, are synthesized by coupling a suitably-protected nucleoside 5'-aldehyde with diphenyl triphenylphosphoranylidenemethylphosphonate to give a α,β-unsaturated phosphonate diester that is then reduced and deprotected at the phosphoryl residue to give the phosphonate. Isosteric nucleoside 3'-phosphonates are synthesized starting from the phosphonylated ribose-1 chloride which is coupled with the heavy metal salt of a purine or pyrimidine. Phosphonates are generally less polar than their phosphate counterparts and therefore are useful as anti-psoriatic agents because they are more readily taken up by cells when applied topically.

(4) Nucleoside Phosphorofluoridates are analogues of mononucleotides. Treatment of nucleoside 5'-phosphates with 2,4-dinitrofluorobenzene produces the nucleoside 5'phosphorofluoridates via the 2,4-dinitrophenylester of the nucleotide.

(5) Other Nucleoside Polyphosphate Analogues include those in which atoms other than oxygen have been substituted between the α,β-phosphorus atoms in di- and triphosphates of nucleosides or between the β,γ-phosphorus atoms in nucleoside triphosphates (including those listed in Table III at page 119 of D. W. Hutchinson, In *Chemistry of Nucleotides and Nucleosides*, L. Townsend, ed., 1991). Usually, the α,β-analogues are prepared by condensing a 2',3'-O-protected nucleoside with the pyrophosphate analogue with the aid of DCC or by nucleophilic displacement reactions involving the displacement of a toluene-sulfonyl (tosyl) residue from the 5'-position of the sugar residue of the tosyl nucleoside by methylene bisphosphonate ion. Preparation of a β,γ-analogue is presented in Example 4.

Preparation of Topical Polyethylene Cream: 5 grams of the nucleoside phosphate is dissolved in 5 ml of propylene glycol and 60 grams of polyethylene glycol 400 (both from Spectrum Chemicals Inc. Los Angeles, Calif.) at 70° with stirring. 40 grams of polyethylene glycol 3350 (Spectrum Chemicals Inc.) is added with stirring until the mixture becomes completely clear. The composition is then placed in tubes or other containers and allowed to cool to room temperature and sealed. The effective concentration of the active ingredient in the composition may be varied from 0.001 gm % to 50 gm % and preferably is from 0.01 gm % to 5 gm %. The composition may also comprise other ingredients for enhancing penetration of the skin (e.g., dimethyl sulfoxide or DMSO) and/or the stability of the composition upon storage as are known to those of ordinary skill in the art.

Treatment of Psoriasis: Topical compositions of the invention comprising an antiproliferative or anti-inflammatory nucleoside phosphate in a psoriasis-effective concentration ranging from 0.01 gm % to 10 gm % are applied to the affected areas from one to six times daily. Dosage schedules and optimal concentrations of the active nucleoside phosphate compounds may be readily determined by physicians skilled in the art of treating psoriasis.

The present invention is described below in additional detail using the following nonlimiting examples. The methods described below are applicable to all methods within the scope of the invention. Therefore, the following preferred embodiments are to be construed as merely illustrative and not limiting in any way.

EXAMPLE 1

PREPARATION OF NUCLEOSIDE TRIPHOSPHATES FROM MONONUCLEOSIDES

Preparations of 5' triphosphates of deoxyribonucleotides, dideoxyribonucleotides and analogs involves a series of reactions as outlined immediately below.

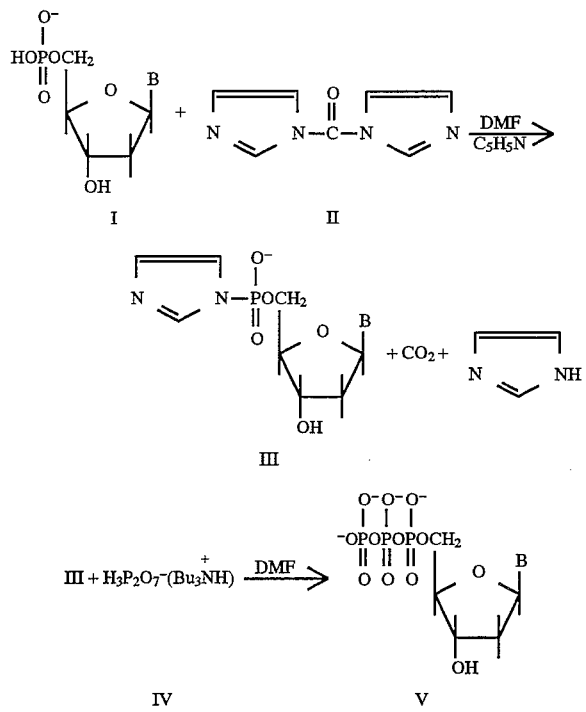

Mononucleotide synthesis is described in the co-pending U.S. patent application Ser. No. 08/060,258, filed May 12, 1993. A nucleotide (I) and excess 1,1'-carbonyldiimidazole (II) are reacted for about 1 hour at room temperature to form an imidazolidate (III). Unreacted 1,1'-carbonyldiimidazole is decomposed with methanol before an excess of inorganic pyrophosphate (IV) is added. This eliminates the formation of inorganic polyphosphates which would have to be subsequently removed from the reaction materials. Phosphorylation is allowed to proceed to completion at about 24 hours after addition of the inorganic pyrophosphate (IV) and then the nucleoside triphosphate product (V) is purified by anion-exchange chromatography on DEAE-cellulose followed by conversion of the product to a salt such as a sodium salt. Because the nucleotide (I) and the imidazolidate (III) can react together to form a symmetrical pyrophosphate by-product, the anion-exchange chromatography on DEAE-cellulose is carried out at a lower pH where the desired product (V) has less charge than the undesirable by-product, thus allowing separation of the two compounds.

One reagent used in the synthesis is tributylammonium pyrophosphate which is made by the following procedure. To an aqueous solution of pyridinium pyrophosphate, obtained by passing a solution of tetrasodium pyrophosphate decahydrate (446 mg, 1 mmole) through a column of Dowex 50W-X4™ (pyridinium) resin (17 ml) is added tributylamine (0.24 ml, 1 mmole). The solution is concentrated under vacuum and the residue is then dried by consecutive addition and evaporation of anhydrous pyridine followed by addition and evaporation of two 10-ml portions of N,N-dimethylformamide (DMF).

The synthesis of nucleoside triphosphates is accomplished by the following method. To a solution or suspension of the mono-oligonucleotide (0.1 mmole) as the anhydrous tributylammonium salt, in 1 ml of DMF, is added 1,1'-carbonyldiimidazole (80 mg, 0.5 mmole) in 1 ml DMF. The combination is mixed for 30 minutes and then held in a desiccator at room temperature for 4–12 hr before it is treated with 33 μl (0.8 mmole) of methanol and allowed to react for 30 min at RT. Tributylammonium pyrophosphate (0.5 mmole) in 5 ml DMF is added and vigorously mixed and then the mixture is held in a desiccator at RT for about 24 hr to allow imidazolium pyrophosphate to precipitate. The precipitate is removed and washed with four 1 ml portions of DMF by centrifugation and resuspension in the DMF resulting in about 80–100% purity. The supernatant is treated with an equal volume of methanol and evaporated to dryness under vacuum. The residue is chromatographed on a 2×20 cm column of DEAE-cellulose with a linear gradient of triethylammonium bicarbonate (a 3 l gradient of about 0 to 0.4M at pH 5–7.5 and fractions are collected and assayed spectrophotometrically to identify fractions containing nucleoside triphosphates. The appropriate fractions are evaporated under vacuum and the triethylammonium nucleoside triphosphate is dissolved in methanol to a concentration of about 0.05M and five volumes of an acetone solution of sodium perchlorate (15 equiv) is added to form a precipitate of the sodium salt of the nucleoside triphosphate. It will be understood by those skilled in the art that other salts of the nucleoside triphosphate could be made by the appropriate precipitation reactions. The precipitated salt is collected by centrifugation, washed with four 1-ml portion of acetone and dried under vacuum over phosphorus pentoxide.

Additional procedures are available for synthesis of nucleoside triphosphates including the one presented in the next example.

EXAMPLE 2

SYNTHESIS OF NUCLEOSIDE MONO-, DI- AND TRI-PHOSPHATES USING 2,2,2-TRIBROMOETHYL PHOSPHOROMORPHOLINOCHLORIDATE

Using the method essentially of van Boom, et al. (Tetrahedron Lett. 32:2779–2782, 1975), mono-, di- and tri-phosphates of ribonucleosides and their derivatives are prepared from a single intermediate. In general, the reactions include reacting a monofunctional reagent (2,2,2-tribromoethyl phosphoromorpholinochloridate) with a ribonucleoside (or its derivative) to make phosphotriester derivatives with a 2,2,2-tribromoethyl protecting group attached to the ribonucleoside (i.e., to produce a ribonucleoside 5'-phosphomorpholidates or ribonucleoside 5'-phosphomorpholidate derivatives). The protecting group is removed by a Cu/Zn coupling reaction with acidic deblocking and neutralization to produce the mono-, di-, and triphosphates depending on the acid used in the deblocking step and the ammonium salt used in the neutralizing step. That is, to obtain the monophosphate ribonucleoside, HCl and ammonia are used; to obtain the diphosphate ribonucleoside, the mono(tri-n-butylammonium) salt of phosphoric acid is used; to obtain the triphosphate ribonucleoside, bis(tri-n-butylammonium) pyrophosphate is used.

The general reactions are diagrammed as follows:

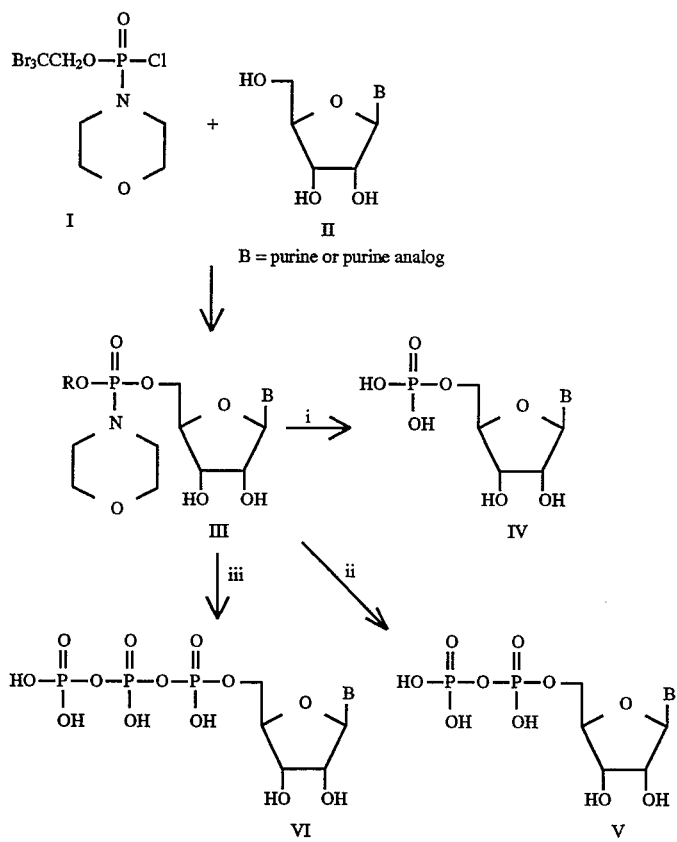

B = purine or purine analog

The monofunctional reagent (I) 2,2,2-tribromoethyl phosphoromorpholinochloridate is prepared by reacting 2,2,2-tribromoethyl phosphorodichloridate and morpholine in anhydrous ether, from which the reaction product is removed and recrystallized using cyclohexane/n-pentane using methods well known in the art. The crystalline 2,2,2-tribromoethyl phosphoromorpholinochloridate has a m.p. of 79° C.

The monofunctional reagent (2 mmole) is mixed with 1 mmole of the nucleoside or its derivatives in anhydrous pyridine at 20° C. for 48 hr; then the reaction mixture is fractionated chromatographically (B. J. Hunt & W. Rigby, Chem. & Ind. 1868, 1967) to yield colorless solids of nucleotides (III). Treatment of the nucleotides with Cu/Zn couple in anhydrous DMF for 10 min at 20° C. followed by filtration to remove excess Cu/Zn gives the nucleoside phosphoromorpholidates.

The nucleoside phosphoromorpholidates are then treated with different acids and ammonia sources to yield either mono-, di-, or tri-phosphates. For monophosphate, the phosphoromorpholidate is treated with 0.01N HCl, pH 2 for 2 hr at 20° C. and then neutralized with aqueous ammonia (pH 9) and purified over a column of SEPHADEX G-25™.

Similarly the nucleoside 5'-triphosphate is obtained by reacting the phosphoromorpholidate (0.1 mmole) in 2 ml of anhydrous DMF with 0.5 mmole of bis(tri-n-butylammonium) pyrophosphate in 2 ml of anhydrous DMF at 20° C. for 3 hr under conditions that exclude moisture. The reaction product is concentrated under vacuum, treated with DOWEX 50™ (ammonium form), and purified on a 2×25 cm column of DEAE cellulose using a 3 l linear gradient of 0.0 to 0.3M $Et_3NH_2CO_2$ solution.

The nucleoside 5'-diphosphate is obtained by reacting the phosphoromorpholidate (0.1 mmole) with 0.6 mmole of mono(tri-n-butylammonium)phosphate in 4 ml of anhydrous pyridine at 20° C. for 3 hr under conditions that exclude moisture and the reaction product is similarly concentrated and purified. Alternatively, the phosphotriester derivatives (III) can be converted directly into the corresponding nucleoside diphosphates by treatment with Zn-dust in pyridine solution containing mono(tri-n-butylammonium) phosphate. That is 1 mmole of reagent III is added to a stirred solution of 15 ml anhydrous pyridine containing 0.1 g of finely divided Zn and 12 mmole mono(tri-n-butylammonium)phosphate under conditions that exclude moisture for about 48 hr at 20° C. Then the reaction mixture is centrifuged to pellet the Zn and the supernatant is co-evaporated three times with 15 ml of water at each step before purification on DEAE cellulose.

EXAMPLE 3

SYNTHESIS OF 7-DEAZAPURINE 2'DEOXYRIBONUCLEOSIDE TRIPHOSPHATES (1) 7-Deaza-2'-deoxinosine 5'-triphosphate, triethylammonium salt, synthesis. 7-Deaza-2'-deoxinosine (25 mg, 0.1 mmol) is dissolved in trimethyl phosphate (250 μl, 1.07 mmol) and POCl₃ (18.5 μl, 0.2 mmol) are added. The mixture is stirred for 1.5 h at 0° C. and then a mixture of 0.5M bis(tri-n-butylammonium) pyrophosphate in 1 ml of anhydrous DMF and 1 ml of tri-n-butylamine are added with vigorous stirring for 1 min.; the solution is neutralized with 1M aqueous $Et_3NH_2CO_3$ solution, pH 7, and evaporated to dryness under vacuum. The residue is purified on a 2.6×30 cm column of DEAE-sephadex using a linear gradient of $Et_3NH_2CO_3$, pH 7 (11 $H_2O$/11 0.7M TBK) solution to yield a colorless solid with a UV ($H_2O$) $\lambda_{max}$ of 258 nm.

(2) 7-Deaza-2'-deoxyadenosine 5'-triphosphate, triethylammonium salt, synthesis. This compound is similarly prepared starting from 7-deaza-2'-deoxyadenosine to yield a colorless solid with a UV ($H_2O$) $\lambda_{max}$ of 270 nm.

(3) 7-Deaza-2'-deoxyguanosine 5'-triphosphate, triethylammonium salt, synthesis. This compound is similarly prepared starting from 7-deaza-2'-deoxyguanosine to yield a colorless solid with a UV ($H_2O$) $\lambda_{max}$ of 259 nm.

EXAMPLE 4

SYNTHESIS OF 2-CHLORODEOXY-3 ADENOSINEPHOSPHOMETHYLENE DIPHOSPHONATE (2CdAPMDP)

Nucleoside polyphosphate analogues have been synthesized in which the atom between the β,γ-phosphorus atoms in a nucleoside triphosphate, such as deoxyadenosine triphosphate, have been replaced by an atom other than oxygen (T. C. Myers et al., Phosphonic analogs of nucleoside phosphates. I. The synthesis of 5'-adenylyl methylene diphosphonate, a phosphonic analog of ATP. *J. Am. Chem. Soc.* 85:3292–3295, 1963; R. G. Yount, ATP analogs, *Adv. Enzymol.* 43:1–56, 1975). The substitution creates a stronger bond than the P—O bond that occurs in a nucleoside phosphate molecule.

The synthesis is essentially as described in Method 1 or Method 2 of Myers et al. (*J. Am. Chem Soc.* 85: 3292–3295, 1963). In Method 1, 2-chlorodeoxyadenosine 5'-phosphoramidate is reacted with methylenediphosphonic acid to produce the phosphonic acid analogs of the nucleoside polyphosphate. Alternatively, using Method 2, 2-chlorodeoxyadenosine monophosphate is reacted with methylenediphosphonic acid using dicyclohexylcarbodiimide (DCC) as the condensing agent.

According to Method 1, methylenediphosphonic acid is obtained by hydrolysis in concentrated HCl of its tetraethyl ester which is prepared by the reaction of methylene iodide with excess triethyl phosphite. 1,3-Dicyclohexylguanidinium adenosine 5'-phosphoramidate (3.6 mmole) and methylenediphosphonic acid (10.8 mmole) are treated with 54 ml of freshly distilled o-chlorophenol; the mixture is cooled on ice and 36 ml of dry pyridine is added. This resulting solution is allowed to stand at RT with occasional shaking for 48 hr when 300 ml of water is added while cooling in ice. The solution is extracted six times with ether (850 ml total). The aqueous solution is adjusted to pH 2 with 1N HCl and then treated with 30 g of acid-washed charcoal (Norit A) and stirred for 30 min; then the charcoal is collected by filtration and washed exhaustively with water (5 l total). The nucleotide derivatives are eluted with 50% aqueous ethanol-5% concentrated ammonium hydroxide (3 l total) and the eluate is concentrated to a 400 ml volume by evaporation at 35° C. The concentrated eluate is applied to a 2.7 cm×31 cm column of Dowex-2™ (chloride; 8% cross linking) and eluted with a linear gradient made from mixing 2 l of 0.003N HCl (in the mixing vessel) and 2 l of 0.003N HCl plus 0.45N LiCl (in the reservoir); 10 ml fractions are collected and fractions containing the 2-chlorodeoxyadenosinephosphomethylenediphosphonate (2CdAPMDP) are identified using paper chromatography or ultraviolet absorbance using methods well known in the art. The 2CdATMDP-containing fraction is neutralized with 1N LiOH and concentrated by evaporation at 30° C.; the concentrated solution is treated with 250 ml of acetone-10% methanol to precipitate a solid which is separated by centrifugation and washed with the acetone-10% methanol mixture until no chloride is detected in the washes. The Li-salt of 2CdATMDP can be further purified by dissolving the salt in 100 ml of water adjusted to pH 8 with LiOH and chromatographing the solution through a DOWEX-2™ column as described above using a gradient made from 1.5 l of 0.003N HCl in the mixing chamber and 1.5 l of 0.003N HCl plus 0.45N LiCl in the reservoir and treating the eluate as described above, followed by dissolving the precipitate in 6 ml water and precipitating it with 40 ml of methanol. The final precipitate is dissolved in 15 ml of water and lyophilized to produce a powder of tetralithium 2CdATMDP.

Using Method 2, methylenediphosphonic acid (11.4 mmole) and 2-chlorodeoxyadenosinemonophosphate (2.6 mmole) are dissolved in pyridine (30 ml) and water (4 ml) to produce a two-phase mixture to which DCC is added at RT with vigorous stirring in three aliquots (29 mmole at the start of the reaction; 48 mmole after 4 hr; and 19 mmole after 12 hr). After 24 hr, the reaction is completed and precipitated dicyclohexylurea is filtered off and washed with water. The filtrate and washings are adjusted to a total volume of 150 ml with water and extracted five times with ether (300 ml total). The solution is adjusted to pH 8 and chromatographed on a 2.5 cm×17.5 cm column of Dowex-1™ (formate; 2% cross linking) column; the column is washed with 1.5 l of water to remove pyridine. Elution from the column is carried out using a gradient created by adding successively to a mixing chamber containing 500 ml water the following solutions: 4N formic acid (500 ml), 4N formic acid plus 0.1M ammonium formate (500 ml), and 4N formic acid plus 0.2M ammonium formate (1500 ml) and collecting 15 ml fractions. The fractions containing 2CdATMDP (approximately in tubes 115–134) are identified using ultraviolet absorption using methods well known in the art. The combined fractions containing 2CdATMDP are lyophilized to a volume of about 200 ml and then treated with 7 g of acid-washed charcoal (Norit A) and stirred for 15 min; then the charcoal is collected by filtration and washed with water (800 ml total). The product is eluted with 50% aqueous ethanol-5% concentrated ammonium hydroxide (600 ml total) and the eluate is concentrated to a 200 ml volume by evaporation at 20° C., filtered to remove trace amounts of charcoal and lyophilized to powder. The powder is dissolved in 4 ml of water and the solution is treated with excess 1M barium acetate; the resulting precipitate is collected by centrifugation, washed water and dissolved in 0.1N HBr at 0° C. The solution is adjusted to pH 6.5 with 1N NaOH and the resulting precipitate is collected by centrifugation, washed with successively with 2-×2 ml each of water, ethanol and ether. The sample is dried at RT over $P_2O_4$ for 12 hr to yield dibarium 2CdATMDP hydrate. Other nucleoside analog phosphomethylenediphosphonates of the invention are prepared similarly.

EXAMPLE 5

APPLICATION OF PHOSPHATE ESTERS HAVING AN ANTI-PROLIFERATIVE EFFECT USING THE EFAD MOUSE MODEL

Mono-, di- and tri-phosphate esters of antiproliferative nucleoside analogs are prepared essentially as described in Example 2. These compounds are individually formulated into topical polyethylene creams as described above containing from 0.001 gm % to 10 gm % of the active ingredient in a cream of propylene glycol, polyethylene glycol 400 and polyethylene glycol 3350 to make a cream mixture. Similar formulations containing an ingredient for enhancing penetration of the skin (e.g., dimethylsulfoxide or AZONE™) are also made.

The compositions are applied in 10 µl aliquots at 6 hour intervals to the dorsal side of EFAD hairless mice over a period of 6 hr to 5 days. At the completion of each time interval, one mouse is killed and the treated tissue is excised and placed into tissue culture medium containing $^3$H-thymidine deoxyribose for pulse labeling for 2 hours to measure the effects of the mono-, di- and tri-phosphate esters of on skin cell proliferation. Then the DNA is isolated from the tissue using standard procedures and the incorporation of $^3$H-thymidine deoxyribose into the DNA is measured by determining the radioactivity (cpm/µg of DNA) in the isolated DNA.

The efficacy of the mono-, di- and tri-phosphate esters of anti-psoriasis compositions for proliferative suppression is determined by comparing the incorporation of radioactivity into DNA from untreated tissue with that of DNA from tissue treated with different formulations of the anti-psoriasis agent.

The total amount of active ingredient for each tested skin biopsy is determined from the gm % of the active ingredient in the cream formulation applied and the number of applications administered before the mouse skin was assayed. For each experimental time point, a corresponding untreated time point is assayed using skin from the ventral side of the same mouse. The difference in incorporation of $^3$H-thymidine deoxyribose into the DNA from the dorsal skin and the control ventral skin is used to calculate the total % suppression of cell proliferation as a function of the total amount of each of the phosphate esters of administered.

The results of $^3$H-incorporation are also used to determine the % suppression (comparing dorsal skin to ventral skin incorporation) as a function of time for each of the individual compositions tested.

As a function of time and as a function of total amount of active ingredient administered, the $^3$H-incorporation into DNA corresponding to dorsal skin treated with phosphate esters of is significantly less than the $^3$H-incorporation into DNA corresponding to the untreated ventral skin.

EXAMPLE 6

APPLICATION OF DIDEOXYCYTIDINE TRIPHOSPHATE INHIBITS POLYAMINE BIOSYNTHESIS IN A MOUSE MODEL

The Polyamine Biosynthesis Inhibition Assay is performed by measuring the amount of ornithine decarboxylase (ODC) present in epidermal cells after topical administration of dideoxycytidine triphosphate to mouse skin previously treated with the phorbol ester 12-O-tetradecanoylphorbol-13-acetate (TPA; applied to increase ODC activity).

Briefly, an athymic nude mouse or EFAD mouse is topically treated with a solution of TPA to increase the level of ODC in the epidermal tissue and mimic the elevated levels of this enzyme as generally found in hyperplasia associated with psoriasis. Within 30 min to 1 hr after TPA treatment, a cream containing dideoxycytidine triphosphate as the active ingredient along with 0.01% DMSO to enhance skin penetration is applied to the TPA treated area of skin.

The cream contains dideoxycytidine triphosphate prepared essentially as disclosed in Example 2 and is prepared in a pharmaceutically acceptable cream at a concentration of 5 gm % which is applied to the skin in an aliquot of 20 µl; additional aliquots are applied every hour for a period of six hours for a total of six applications. At the end of the six hours, ODC levels in the skin are determined using techniques well known in the art (J. Lesiewicz et al., In *Models in Dermatology*, vol. 2 (H. I. Maibach & N. J. Lowe, eds.), 1985, pp 112–116). As controls, untreated skin from a nude athymic mouse is tested to determine normal levels of ODC and skin from a nude athymic mouse treated with TPA is tested to determine the level of ODC elevation following TPA administration. As a further control, normal and TPA treated skin is treated in parallel with the cream formulation containing DMSO but without dideoxycytidine triphosphate.

The ODC level in skin treated with TPA and the dideoxycytidine triphosphate containing cream is compared to that of normal skin and to that in TPA-treated skin. The efficacy of dideoxycytidine triphosphate treatment is determined by the decrease in ODC relative to that seen in TPA-treated skin and by the level of ODC relative to normal skin. After treatment with the dideoxycytidine triphosphate containing cream, the ODC levels are significantly decreased relative to ODC levels in TPA-treated skin that received no cream or that received cream without the dideoxycytidine triphosphate as an active ingredient.

It will be understood by those skilled in the art that similar treatment and analysis of the efficacy of treatment with other dideoxynucleoside phosphate esters can be similarly determined. These dideoxynucleoside phosphate esters include mono-, di- and tri-phosphate esters of dideoxythymidine, dideoxyguanosine, dideoxyadenosine, dideoxyinosine, and dideoxynucleoside analogs including azidodideoxythymidine (AZT) and dideoxydidehydrothymidine.

EXAMPLE 7

APPLICATION OF PHOSPHATE ESTERS OF 5-FLUORODEOXYURIDINE AND 5-FLUOROURIDINE HAVING AN ANTI-PROLIFERATIVE EFFECT USING A MOUSE ENGRAFTED WITH PSORIATIC HUMAN SKIN

A skin biopsy is used to detect the anti-proliferative effect of 5-fluorodeoxyuridine triphosphate and 5-fluorouridine triphosphate when applied topically to human psoriatic skin engrafted onto an athymic mouse. Human psoriatic skin of about 1–10 mm in diameter is engrafted onto the dorsal side of an athymic mouse using well known techniques in the art. After the graft has sufficiently healed, the psoriatic human skin is treated with a anti-psoriatic pharmaceutical containing as an active ingredient 5-fluorodeoxyuridine triphosphate, 5-fluorouridine triphosphate or their mono- or di-phosphates. These compounds are synthesized essentially as described in Example 1. The pharmaceutical compositions are made by including the active ingredients in a topical polyethylene cream essentially as described earlier in the disclosure with the active ingredients at a concentration of 0.1 gm % to 10 gm %. The cream containing the active ingredients is applied to the engrafted skin sections in 20 µl aliquots at intervals of 6 hours over 1–15 days. After each 24 hour period of treatment, the treated skin is examined for gross indications of psoriasis (flakiness of skin and redness of inflammation). After the 15th day, the skin is removed from the mouse and biopsies are used to determine the number of epidermal cell layers and the relative degree of dilation of the capillaries within the skin by microscopic inspection using standard histological techniques.

The number of epidermal cell layers is compared to similarly examined normal human and untreated human psoriatic skin that has been grafted to athymic nude mice to determine the effect of the treatment with the 5-fluorodeoxyuridine triphosphate and 5-fluorouridine triphosphate containing pharmaceutical compositions. The relative degree of inflammation in the tissue is quantitated by determining the number of neutrophils and monocytes in the capillaries of the dermis under appropriate staining conditions. The relative degree of dilation of the capillaries compared to untreated psoriatic skin and normal control skin is noted.

The number of layers of cells in the epidermis, the degree of inflammation and the degree of capillary dilation is correlated to the day of treatment and the amount of active ingredient as determined from the concentration in the composition and the amount administered. The compositions having 5-fluorodeoxyuridine triphosphate, 5-fluorouridine triphosphate or their mono- or di-phosphates all show significant reduction in the symptoms of psoriasis relative to untreated psoriatic skin.

EXAMPLE 8

APPLICATION OF 7-DEAZAPURINE 2'DEOXYRIBONUCLEOSIDE TRIPHOSPHATES HAVING AN ANTI-PROLIFERATIVE EFFECT ON PSORIATIC HUMAN SKIN

A human volunteer having patches of psoriatic flaky skin on both forearms is treated with a cream composition including as an active ingredient a triethylammonium salt of 7-deaza-2'-deoxinosine 5'-triphosphate, synthesized essentially as described in Example 3. The active ingredient is at a concentration of 50 gm % in a pharmaceutically acceptable cream such as the polyethylene glycol cream described earlier in the disclosure.

The skin on both arms is examined macroscopically for flakiness and inflammation and the results are recorded (written observations and photographs) before beginning treatment with the 7-deaza-2'-deoxinosine 5'-triphosphate containing cream. One or two drops of the cream is applied to areas of the psoriatic skin of about 3 cm in diameter on one of the forearms at 6 hour intervals over the course of 14 days. The other forearm remains untreated during the 14 day period.

At daily intervals during the 14 day period, the skin on both arms is examined macroscopically for flakiness and inflammation and the results are recorded as above for bilateral paired comparisons. If sufficient amount of psoriatic patches are available on the human volunteer, similar compositions containing triethylammonium salts of 7-deaza-2'-deoxyadenosine 5'-triphosphate and 7-deaza-2'-deoxyguanosine 5'-triphosphate at a concentration of 50 gm % are simultaneously tested for anti-psoriatic activity.

At the end of the 14 day period, a 1–2 mm diameter section of dermis and epidermis is removed for biopsy and microscopic examination (to determine the number of layers of cells in the epidermis, the degree of inflammation and the degree of capillary dilation in the dermis) as described in Example 7 using standard histological procedures. Skin is taken from the psoriatic skin of the untreated arm as a negative control, from normal skin of the untreated arm as a positive control, and from the areas treated with the 7-deazapurine 2'deoxyribonucleoside triphosphate containing creams for determination of efficacy of the active ingredients relative to the control samples.

The macroscopic observations of the bilaterally paired areas of treated psoriatic skin and untreated psoriatic skin on the same volunteer show that treatment with the 7-deazapurine2'deoxyribonucleoside triphosphates significantly decreases the symptoms of psoriasis over a 14 day period. The macroscopic observations are supported by results of microscopic examination of skin taken from treated and untreated areas. Similarly, the mono- and di-phosphates also exhibit activity.

EXAMPLE 9

APPLICATION OF PHOSPHATE ESTERS OF 2-CHLORODEOXYADENOSINE HAVING AN ANTI-PROLIFERATIVE EFFECT ON SKIN OF THE FLAKY SKIN MOUSE

Inbred fsn/fsn mice at 35–42 days of age, showing epidermal hyperplasia with inflammation, are treated with a pharmaceutical composition containing as the active ingredient either the mono-, di- or tri-phosphate ester of 2-chlorodeoxyadenosine, prepared essentially as described in Example 2. The composition contains the mono-, di- or tri-phosphate active ingredient at a concentration of 5 gm %. The composition is applied in 5 µl aliquots at 12 hour intervals to a 1–5 mm portion of the ventral skin of fsn/fsn mice; control fsn/fsn mice are similarly treated with the composition lacking the active ingredient. The skin is observed grossly and microscopically at daily intervals beginning 12 hr after the first application and extending up to 15 days later. The observations are used to determine the degree of epidermal hyperplasia and inflammation characteristic of psoriatic skin presented using standard dermatological and histological methods.

For each observation point following treatment, the treated skin is compared to a similar portion of the same mouse that was not treated and to skin treated with just the carrier ingredients without the mono-, di- or tri-phosphate ester of 2-chlorodeoxyadenosine. After a few days, significant improvement in the inflammation and flakiness of the skin is observed for the portions of skin treated with compositions containing either the mono-, di- or tri-phosphate ester of 2-chlorodeoxyadenosine compared to untreated skin or skin treated with the composition lacking the active ingredients.

Similar analysis is performed using the fsn/fsn mice treated with compositions containing as an active ingredient either the mono-, di- or tri-phosphate ester of 2-chloro-2'-fluoroaradeoxyadenosine. Similar reduction in psoriatic symptoms is seen using these compositions over a period of 14 days.

EXAMPLE 10

APPLICATION OF 6-AZAURIDINE TRIPHOSPHATE HAVING AN ANTI-PROLIFERATIVE EFFECT ON PSORIATIC HUMAN SKIN

A human volunteer having patches of psoriatic skin on the arms and legs is treated with a cream composition including as an active ingredient 6-azauridine triphosphate, synthesized essentially as described in Example 1. The active ingredient is at a concentration of 25 gm % in a pharmaceutically acceptable cream such as a polyethylene glycol based cream.

The skin on the arms and legs is examined macroscopically for flakiness and inflammation and the observations are recorded (written and photographed) before beginning treatment with the 6-azauridine triphosphate containing cream. Metered aliquots of the cream, each containing 50 µl, are applied to areas of the psoriatic skin of about 5–10 cm in diameter on one of the arms and one of the legs at 3 hour intervals over the course of 14 days. The other arm and leg remain untreated during the 14 day period to serve as negative controls.

At daily intervals during the 14 day period, the skin on the arms and legs is examined macroscopically for flakiness and inflammation and the results are recorded as above for the bilateral paired comparisons.

At the end of the 14 day period, a 1–2 mm diameter section of skin (dermis and epidermis) is removed for biopsy and microscopic examination to determine the number of layers of cells in the epidermis, the degree of inflammation and the degree of capillary dilation in the dermis as described in Example 7 using standard histological procedures. Skin is taken from the psoriatic skin of the untreated arm and/or leg as a negative control, from normal skin of an untreated area as a positive control, and from the areas treated with the 6-azauridine triphosphate containing cream for determination of efficacy of the active ingredient relative to the control samples.

The macroscopic observations of the bilaterally paired areas of treated psoriatic skin and untreated psoriatic skin on the same volunteer show that treatment with the 6-azauridine triphosphate significantly decreases the symptoms of psoriasis over a 14 day period. The macroscopic observations are supported by results of microscopic examination of skin taken from treated and untreated areas. Similar results are obtained with the mono- and di-phosphates of 6-azauridine.

EXAMPLE 11

TREATMENT OF HUMAN PSORIATIC SKIN USING 2-CHLORODEOXYADENOSINEPHOSPHOMETHYLENE DIPHOSPHONATE (2CdATMDP)

Human psoriatic skin grafted onto an athymic nude mouse is used to detect the anti-proliferative effect of 2CdATMDP when applied topically. Macroscopic observation and microscopic skin biopsy analysis is used to detect efficacy of the anti-psoriatic composition. Human psoriatic skin of about 1–10 mm in diameter is engrafted onto the dorsal side of an athymic mouse using well known techniques in the art. After the graft has sufficiently healed, the psoriatic human skin is treated with an anti-psoriatic pharmaceutical containing as an active ingredient the nucleoside analogue 2CdATMDP, synthesized essentially as described in Example 4. The pharmaceutical composition includes the active ingredient in a topical polyethylene cream essentially as described earlier in the disclosure with the active ingredient at a concentration of about 0.5 gm % to 5 gm %. The cream containing the active ingredient is applied to the engrafted skin sections in 10 µl aliquots at intervals of 12 hours over 1–30 days. The treated skin is examined for gross indications of psoriasis (e.g., flakiness and inflammation) once during every 24 hour period of treatment. At the 15th day and the 30th day, skin is removed from engrafted area of the mouse and standard histological analysis is used to determine the number of epidermal cell layers and the relative degree of dilation of the capillaries within dermis of the skin.

The number of epidermal cell layers is compared to similarly examined normal human and untreated human psoriatic skin that has been grafted to athymic nude mice to determine the effect of the treatment with the pharmaceutical composition containing 2CdATMDP. In addition to the relative degree of dilation of the capillaries, inflammation in the tissue is quantitated by determining the number of neutrophils and monocytes in the capillaries of the dermis compared to untreated psoriatic skin and normal control skin.

The number of layers of cells in the epidermis, the degree of inflammation and the degree of capillary dilation is correlated to the day of treatment and the amount of active ingredient (determined from the concentration in the composition and the amount administered). After the entire treatment period, a significant decrease in inflammation and flakiness is observed in the treated grafted psoriatic skin compared to untreated control psoriatic skin grafted to an athymic nude mouse.

A human volunteer with psoriatic patches of skin on both forearms is similarly treated on one forearm twice per day (using 50 µl per treatment) of the pharmaceutical composition containing the nucleoside analogue 2CdATMDP. The condition of the treated psoriatic skin compared to control areas of the other forearm (untreated skin or skin treated with the cream formulation lacking the active ingredient), is observed daily and a biopsy of skin of about 1–3 mm in diameter is taken at day 15 and day 30 for standard histological analysis as described above for the mouse model. After 15 days, less inflammation is observed in the skin treated with the composition containing 2CdATMDP compared to untreated skin or skin treated with just the formulation's inert mixture without the active ingredient. After the 30th day, a significant change in both inflammation and flakiness is observed in the skin treated with the composition containing the active ingredient compared to control patches of skin from the other forearm.

EXAMPLE 12

TREATMENT OF HUMAN ATOPIC DERMATITIS WITH 2-CHLORO-2'-FLUOROARADEOXYADENOSINE PHOSPHATE ESTER

The mono-, di- or tri-phosphate esters of 2-chloro-2'-fluoroaradeoxyadenosine are synthesized essentially as described in Example 2. An adolescent patient with atopic dermatitis of unknown origin characterized with extreme itching and lesions of eczema on the wrists and neck is treated with a lotion composition containing a mixture of mono-, di- and tri-phosphate esters of 2-chloro-2'-fluoroaradeoxyadenosine, each at a concentration of 5 gm %. The lotion is applied to affected areas of the skin at will up to 12 times per day in portions of about 1–3 cc. After 1–4 weeks of treatment, the itchiness and inflammation of the skin with dermatitis is significantly decreased relative to when the patient presented. Furthermore, after treatment, the eczema lesions on the treated skin are healing or have healed. Thereafter, the lotion is applied at will only when itchiness recurs.

EXAMPLE 13

TREATMENT OF LICHEN PLANUS DISEASE WITH DIDEOXY NUCLEOSIDE PHOSPHATES

The mono-, di- or tri-phosphate esters of dideoxycytidine are synthesized essentially as described in Example 2. Each phosphate ester of dideoxycytidine is formulated into a polyethylene glycol-based cream composition at a concentration of 0.5 gm %. Human volunteers having chronic lichen planus characterized by inflammation and pruritic cutaneous eruptions of papules on their arms and legs are divided into three groups and each group is treated with one of the compositions: the mono-, di- or tri-phosphate esters of dideoxycytidine. Each group is treated using the cream on only one leg or one arm, leaving the other leg or arm untreated as a bilateral control for comparision to the treated skin. The cream is applied in about 1 cc volumes at about 6 hour intervals for a period of 7 days to 3 months. The treated and untreated areas are visually examined daily for the two weeks and thereafter at least weekly or as needed (determined by the treating physician). As inflammation and/or papule formation appears to diminish, the treating physician may also decrease the number of applications per day as needed to maintain control of the disease.

At the time when, in the treated area, inflammation appears to be diminished and the number of pruritic cutaneous eruptions appears to have decreased, a biopsy of skin (about 1–3 mm) is taken from the volunteer from both the treated limb and the untreated limb in the affected area for histological examination for both inflammation (e.g., dilation of dermis capillaries) and characteristics of the papules (e.g., number of layers of epidermis and evidence of whitish lines or puncta associated with the papules).

For each of the three groups, some members of the group show significant improvement in the inflammation and pruritic cutaneous eruptions of papules of lichen planus on the skin of their treated arm or leg compared to the skin on the corresponding untreated limb.

It will be understood by those skilled in the art that similar phosphate esters of other nucleoside phosphate analogs of the invention and dideoxy compounds including dideoxythymidine, dideoxyguanosine, dideoxyadenosine, dideoxyinosine, and dideoxynucleoside analogs including AZT and d4T could similarly be used in pharmaceutical compositions.

EXAMPLE 14

TREATMENT OF ACTINIC KERATOSIS WITH ACYCLOVIR PHOSPHATES

Acyclovir triphosphate is synthesized essentially as described in Example 1 and a cream composition containing 0.1–0.5 gm % of the acyclovir triphosphate and about 0.01 gm % of Azone™ to enhance skin penetration is formulated using methods well known in the art.

A group of middle-aged human volunteers with patches of actinic keratosis on skin that is exposed to the sun (e.g., on the nose, hands, arms or legs) are divided into three groups: one group in which the actinic keratosis is frozen with liquid nitrogen to kill cells, one group which is treated with the acyclovir triphosphate composition and one control group which is treated with the composition containing inert ingredients and AZONE™ but not containing acyclovir triphosphate.

The groups treated with the cream compositions with or without acyclovir triphosphate apply the cream twice per day (morning and evening) in volumes sufficient to cover the affected area (about 0.01–0.5 cc) for a period of up to one month. The treated skin of each group is visually examined every other day by the clinician and the observations recorded (written and photographed). Following treatment, the volunteers are examined every 6 months for recurrence of actinic keratosis in the treated areas.

For the group treated with the cream containing acyclovir triphosphate a significant number of patients show decreased keratotic growth and diminished reddening of the affected area at the end of 1 month of treatment. Treatment can be continued as determined by the clinician based on the 6-monthly checkups. It will be understood by those skilled in the art that mono- and di-phosphates of acyclovir could also be used in similar pharmaceutical formulations, and that mono-, di-, and tri-phosphates of gancyclovir or the other antiproliferative nucleoside analogs of the invention could also be used in compositions having anti-proliferative activity for diseases of the skin associated with hyperproliferation.

For the group treated with the cream composition without acyclovir triphosphate, no change in the actinic keratosis is observed after 1 month and the affected area is then removed using clinically acceptable methods.

For the group treated by freezing the keratotic area with liquid nitrogen, all show death of the cells in the treated area within 24 hours followed by sloughing of the dead cells and associated pain during healing. In some cases, scarring is seen in the treated area.

Although the present invention has been described in the context of particular examples and preferred embodiments, it will be understood that the invention is not limited to such embodiments. Instead, the scope of the present invention shall be measured by the claims that follow. All modifications which come within the meaning and range of the lawful equivalency of the claims are to be embraced within their scope.

We claim:

1. A method for treating a mammal with a disease characterized by hyperproliferation of skin cells comprising topically applying an effective amount of 2-chlorodeoxyadenosine monophosphate ester or pharmaceutically acceptable salt to the affected area of skin.

2. A method for treating a mammal having psoriasis comprising topically applying an effective mount of 2-chlorodeoxyadenosine monophosphate ester or a pharmaceutically acceptable salt thereof to the affected area of skin.

3. A method according to claim 1 or 2 wherein said 2-chlorodeoxyadenosine monophosphate ester or pharmaceutically acceptable salt thereof is applied in a concentration of from about 0.001 gm % to 100 gm % in a carrier suitable for topical use.

4. A method for treating a mammal with a disease characterized by hyperproliferation of skin cells comprising topically applying an effective amount of 2-chloro-2'-arabino-fluoro-2'-deoxyadenosine monophosphate ester or a pharmaceutically acceptable salt thereof to the affected area of skin.

5. A method for treating a mammal having psoriasis comprising topically applying an effective amount of 2-chloro-2'-arabino-fluoro-2'-deoxyadenosine monophosphate ester or a pharmaceutically acceptable salt thereof to the affected area of skin.

6. A method according to claim 4 or 5 wherein said 2-chloro-2'-arabino-fluoro-2'-deoxyadenosine monophosphate ester or pharmaceutically acceptable salt thereof is applied in a concentration of from about 0.001 gm % to 100 gm % in a carrier suitable for topical use.

7. A method for treating a mammal with a disease characterized by hyperproliferation of skin cells comprising topically applying an effective amount of a 2-chlorodeoxyadenosine phosphate ester or a pharmaceutically acceptable salt thereof to the affected area of skin.

8. A method for treating a mammal having psoriasis comprising topically applying an effective mount of a 2-chlorodeoxyadenosine phosphate ester or a pharmaceutically acceptable salt thereof to the affected area of skin.

9. A method according to claim 7 or 8 comprising topically applying an effective amount of 2-chlorodeoxyadenosine diphosphate or a pharmaceutically acceptable salt thereof to the affected area of skin.

10. A method according to claim 7 or 8 comprising topically applying an effective amount of 2-chlorodeoxyadenosine triphosphate or a pharmaceutically acceptable salt thereof to the affected area of skin.

11. A method for treating a mammal with a disease characterized by hyperproliferation of skin cells comprising topically applying a composition containing an effective mount of a 2-chloro-2'-arabino-fluoro-2'-deoxyadenosine phosphate ester or a pharmaceutically acceptable salt thereof to the affected area of skin.

12. A method for treating a mammal having psoriasis comprising topically applying a composition containing an effective amount of a 2-chloro-2'-arabino-fluoro-2'-deoxyadenosine phosphate ester or a pharmaceutically acceptable salt thereof to the affected area of skin.

13. A method according to claim 11 or 12 comprising topically applying a composition containing an effective mount of 2-chloro-2'-arabino-fluoro-2'-deoxyadenosine diphosphate or a pharmaceutically acceptable salt thereof to the affected area of skin.

14. A method according to claim 11 or 12 comprising topically applying a composition containing an effective mount of 2-chloro-2'-arabino-fluoro-2'-deoxyadenosine triphosphate or a pharmaceutically acceptable salt thereof to the affected area of skin.

15. A method according to any one of claims 1, 4, 7 or 10, wherein the treated hyperproliferative skin disease is selected from the group consisting of atopic dermatitis, lichen planus, actinic keratosis, basal cell carcinoma, and squamous cell carcinoma.

16. A method according to any one of claims 1, 2, 4, 5, 7, 8, 11, 12, wherein the affected individual is a human being.

17. A pharmaceutical formulation comprising an effective antiproliferative amount of 2-chlorodeoxyadenosine monophosphate ester or pharmaceutically acceptable salt thereof in a carrier suitable for topical use.

18. A pharmaceutical formulation comprising an effective antipsoriasis amount of 2-chlorodeoxyadenosine monophosphate ester or pharmaceutically acceptable salt thereof in a carrier suitable for topical use.

19. The pharmaceutical formulation of claim 17 or 18 wherein the concentration of 2-chlorodeoxyadenosine monophosphate ester or pharmaceutically acceptable salt thereof is from about 0.001 gm % to 50 gm %.

20. The pharmaceutical formulation of claim 17 or 18 wherein the concentration of 2-chlorodeoxyadenosine monophosphate ester or pharmaceutically acceptable salt thereof is from about 0.01 gm % to 10.0 gm %.

21. The pharmaceutical formulation of claim 17 or 18 wherein the concentration of 2-chlorodeoxyadenosine monophosphate ester or pharmaceutically acceptable salt thereof is from about 0.1 gm % to 1.0 gm %.

22. A pharmaceutical formulation according to claim 17 or 18 wherein said carrier comprises an aqueous cream.

23. A pharmaceutical formulation according to claim 17 or 18 further comprising propylene glycol, polyethylene glycol 400 or polyethylene glycol 3350.

24. A pharmaceutical formulation according to claim 17 or 18 further comprising an ingredient for enhancing penetration of the skin during topical use.

25. A pharmaceutical formulation comprising an effective antiproliferative amount of 2-chloro-2'-arabino-fluoro-2'-deoxyadenosine monophosphate ester or pharmaceutically acceptable salt thereof in a carrier suitable for topical use.

26. A pharmaceutical formulation comprising an effective antipsoriasis amount of 2-chloro-2'-arabino-fluoro-2'-deoxyadenosine monophosphate ester or pharmaceutically acceptable salt thereof in a carrier suitable for topical use.

27. The pharmaceutical formulation of claim 25 or 26 wherein the concentration of the 2-chloro-2'-arabino-fluoro-2'-deoxyadenosine monophosphate ester or pharmaceutically acceptable salt thereof is from about 0.001 gm % to 50 gm %.

28. The pharmaceutical formulation of claim 25 or 26 wherein the concentration of the 2-chloro-2'-arabino-fluoro-2'-deoxyadenosine monophosphate ester or pharmaceutically acceptable salt thereof is from about 0.01 gm % to 10.0 gm %.

29. The pharmaceutical formulation of claim 25 or 26 wherein the concentration of the 2-chloro-2'-arabino-fluoro-2'-deoxyadenosine monophosphate ester or pharmaceutically acceptable salt thereof is from about 0.1 gm % to 1.0 gm %.

30. A pharmaceutical formulation according to claim 25 or 26 wherein said carrier comprises an aqueous cream.

31. A pharmaceutical formulation according to claim 25 or 26 further comprising propylene glycol, polyethylene glycol 400 or polyethylene glycol 3350.

32. A pharmaceutical formulation according to claim 25 or 26 further comprising an ingredient for enhancing penetration of the skin during topical use.

33. A pharmaceutical formulation comprising an effective antiproliferative amount of a 2-chlorodeoxyadenosine phosphate ester or a pharmaceutically acceptable salt thereof in a carrier suitable for topical use.

34. A pharmaceutical formulation according to claim 33 comprising an effective antiproliferative amount of 2-chlorodeoxyadenosine diphosphate or a pharmaceutically acceptable salt thereof in a carrier suitable for topical use.

35. A pharmaceutical formulation according to claim 33 comprising an effective antiproliferative amount of 2-chlorodeoxyadenosine triphosphate or a pharmaceutically acceptable salt thereof in a carrier suitable for topical use.

36. A pharmaceutical formulation comprising an effective antiproliferative amount of a 2-chloro-2'-arabino-fluoro-2'-deoxyadenosine phosphate ester or a pharmaceutically acceptable salt thereof in a carrier for topical use.

37. A pharmaceutical formulation according to claim 36 comprising an effective antiproliferative amount of 2-chloro-2'-arabino-fluoro-2'-deoxyadenosine diphosphate or a pharmaceutically acceptable salt thereof in a carrier suitable for topical use.

38. A pharmaceutical formulation according to claim 36 comprising an effective antiproliferative amount of 2-chloro-2'-arabino-fluoro-2'-deoxyadenosine triphosphate or a pharmaceutically acceptable salt thereof in a carrier suitable for topical use.

39. A pharmaceutical formulation according to claim 33 wherein the concentration of 2-chlorodeoxyadenosine phosphate ester or pharmaceutically acceptable salt thereof is from about 0.001 gm % to 100 gm %.

40. A pharmaceutical formulation according to claim 36 wherein the concentration of the 2-chloro-2'-arabino-fluoro-2'-deoxyadenosine phosphate ester or pharmaceutically acceptable salt thereof is from about 0.001 gm % to 100 gm %.

* * * * *